(12) United States Patent
Cunningham et al.

(10) Patent No.: US 8,062,332 B2
(45) Date of Patent: Nov. 22, 2011

(54) SURGICAL COBRA HEAD SUTURE NEEDLE

(75) Inventors: Scott Cunningham, Cheshire, CT (US); Stanislaw Z. Marczyk, Stratford, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 645 days.

(21) Appl. No.: 10/618,990

(22) Filed: Jul. 14, 2003

(65) Prior Publication Data
US 2004/0098048 A1 May 20, 2004

Related U.S. Application Data

(60) Provisional application No. 60/396,444, filed on Jul. 17, 2002.

(51) Int. Cl.
*A61B 17/06* (2006.01)
(52) U.S. Cl. .......................... 606/223; 606/222
(58) Field of Classification Search .................. 606/172, 606/222–224; 604/272–274; 112/222; 30/353
See application file for complete search history.

(56) References Cited

U.S. PATENT DOCUMENTS

| | | | |
|---|---|---|---|
| 20,409 A | 6/1858 | Cottrill | |
| 461,602 A | 10/1891 | Boult | |
| 722,105 A | 3/1903 | Hervey | |
| 1,599,059 A | 9/1926 | Morton | |
| 2,838,049 A | 6/1958 | Eisenhofer | |
| 2,841,150 A | 7/1958 | Riall | |
| 3,038,475 A | 6/1962 | Orcutt | |
| 3,238,942 A | 3/1966 | Lincoff | |
| 4,513,747 A * | 4/1985 | Smith | 606/223 |
| 4,524,771 A | 6/1985 | McGregor et al. | |
| 4,527,564 A | 7/1985 | Eguchi et al. | |
| 4,537,593 A * | 8/1985 | Alchas | 604/411 |
| 4,565,545 A * | 1/1986 | Suzuki | 604/164.06 |
| 4,660,559 A | 4/1987 | McGregor et al. | |
| 4,799,484 A * | 1/1989 | Smith et al. | 606/223 |
| 4,932,961 A | 6/1990 | Wong et al. | |
| 5,002,564 A | 3/1991 | McGregor | |
| 5,002,565 A | 3/1991 | McGregor | |
| 5,030,228 A * | 7/1991 | Wong et al. | 606/223 |
| 5,057,082 A * | 10/1991 | Burchette, Jr. | 604/164.06 |
| 5,089,012 A | 2/1992 | Prou | |
| 5,100,431 A | 3/1992 | Buster et al. | |
| 5,178,628 A | 1/1993 | Otsuka et al. | |
| 5,330,441 A | 7/1994 | Prasad et al. | |

(Continued)

OTHER PUBLICATIONS

International Search Report (PCT/US05/02845 dated Mar. 19, 2007).

*Primary Examiner* — Corrine M McDermott
*Assistant Examiner* — Melissa Ryckman

(57) ABSTRACT

A surgical needle includes an elongated needle body defining a longitudinal y-axis along which the needle body extends and transverse x and z-axes. The needle body includes a central shaft portion, a first suture end portion for attachment to a suture and a second needled end portion for penetrating tissue. The needled end portion has three sides which intersect to define three cutting edges and terminate at a needle point. At least one side includes a pair of planar surface portions arranged in oblique relation to define a general concave appearance to the one side. The needled end portion further defines an enlarged transition portion adjacent the central shaft portion with at least an x-dimension greater than a corresponding x-dimension of the central shaft portion.

17 Claims, 2 Drawing Sheets

U.S. PATENT DOCUMENTS

| | | |
|---|---|---|
| 5,342,397 A | 8/1994 | Guido |
| 5,403,344 A * | 4/1995 | Allen .................... 606/223 |
| 5,464,422 A | 11/1995 | Silverman |
| 5,693,072 A | 12/1997 | McIntosh |
| 5,693,454 A | 12/1997 | Munoz |
| 5,730,732 A * | 3/1998 | Sardelis et al. ........... 604/272 |
| 5,733,266 A * | 3/1998 | Gravlee, Jr. ............. 604/272 |
| 5,762,811 A | 6/1998 | Munoz |
| 5,776,268 A | 7/1998 | McJames et al. |
| 5,797,961 A * | 8/1998 | Smith et al. ............. 606/222 |
| 5,820,609 A * | 10/1998 | Saito ..................... 604/272 |
| 6,322,581 B1 | 11/2001 | Fukuda et al. |
| 2003/0074022 A1 | 4/2003 | Roby |

\* cited by examiner

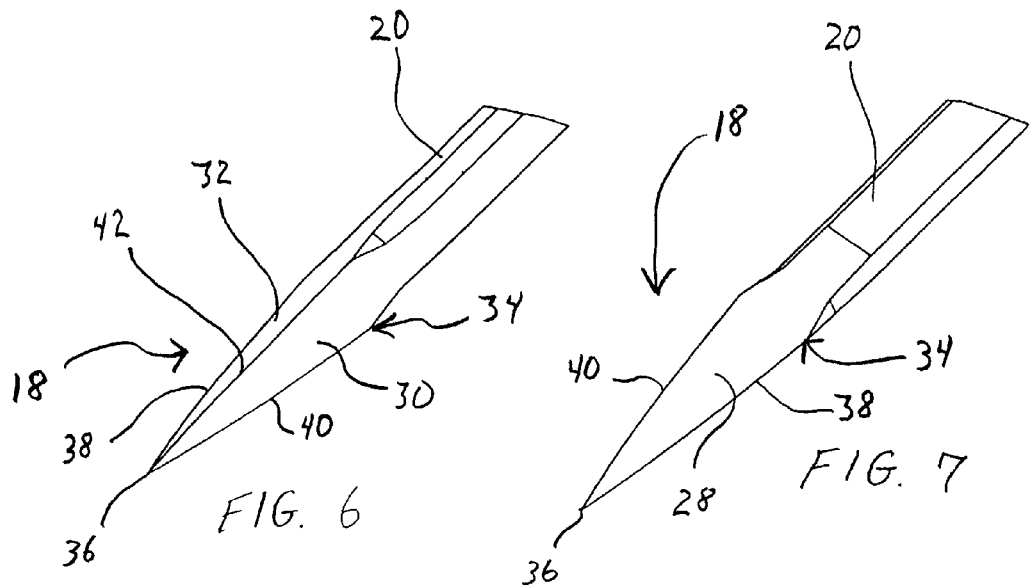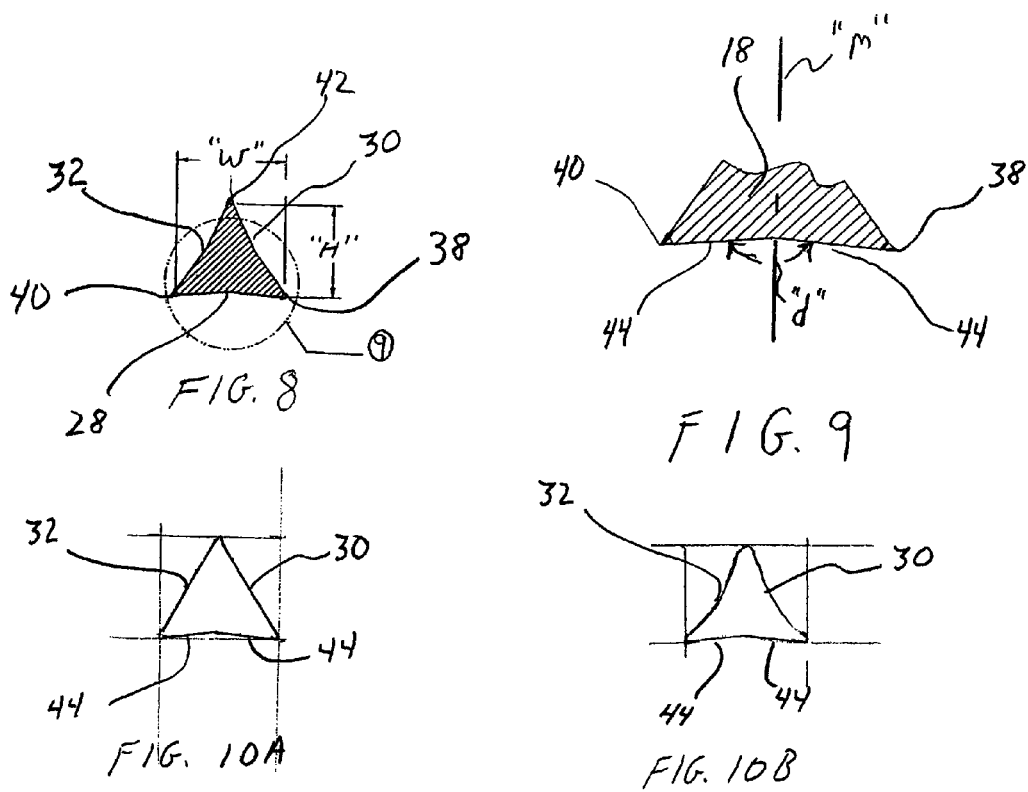

SURGICAL COBRA HEAD SUTURE NEEDLE

This application claims benefits of and priority to U.S. Provisional Patent Application Ser. No. 60/396,444 entitled "SURGICAL COBRA HEAD SUTURE NEEDLE" which was filed on Jul. 17, 2002, the entire contents of which are hereby incorporated by reference herein.

TECHNICAL FIELD

The present disclosure relates to a surgical suturing needle for suturing cutaneous and subcutaneous tissue, and in particular, relates to a surgical needle having a mulitifaceted penetrating needle end characterized by enhanced penetrability and reduced tissue drag.

BACKGROUND OF RELATED ART

Suturing needles for applying sutures, or stitches, by hand in cutaneous and subcutaneous tissue are well known in the art. Typically, the sutures are used to close wounds or adjoin adjacent tissue, often at the conclusion of a surgical procedure. Suturing needles are usually made from a cut blank of material such as stainless steel. The cut blank is metal-worked using well known machining techniques to form the surgical suturing needle. The needle generally includes a shaft, a rear end portion with an aperture or channel to secure a suturing thread and a needle head at a front end portion for puncturing skin and tissue through which the needle travels. The needle head typically incorporates a sharpened needle tip at its distal end and cutting edges. Alternatively, the needle tip may be of a tapered configuration. Straight and curved needles including multiple curved configurations are also known in the art.

An important consideration in the design of surgical suturing needles is needle sharpness. Sharper needles require less force to penetrate tissue and thus cause less tissue trauma. In addition, a sharper needle reduces fatigue on the needle itself, making it less likely to bend or break during suturing. Needle sharpness is typically defined in terms of "penetration force"—the force necessary for a needle to puncture, or penetrate, the tissue. The penetration force is primarily determined by the design and sharpness of the needle point and the cutting edges formed on the needle head. Needle sharpness is also affected by drag force on the needle as it travels through the tissue. The drag force depends upon the design and sharpness of the needle, and the presence of a lubricating coating.

Another important consideration in needle design and manufacture is to maximize resistance to bending or breaking during use. The strength of a suturing needle is a measure of its ability to resist bending and is determined by such factors as (a) the material of fabrication, (b) the cross-sectional shape of the needle, and (c) the heat treatment applied to the needle during manufacturing. Needle strength should be balanced by needle ductility, which is defined in terms of the ability of the needle to be reshaped after it flexes from its original shape. A surgical needle with good strength characteristics but little or no ductility can be brittle, and may snap and break during use. It is generally known that in working with a metallic material, as the strength of the material increases the ductility will decrease. Therefore, it is desirable to carefully balance the strength and ductility characteristics of a suturing needle.

SUMMARY

Accordingly, the present disclosure is directed to further advancements in surgical suturing needles. The surgical needle of the present disclosure possesses enhanced needle attributes including needle sharpness, resistance to bending or breaking during use and reduced tissue drag. In one embodiment, a surgical needle, includes an elongated needle body defining a longitudinal y-axis along which the needle body extends and transverse x and z-axes. The needle body includes a central shaft portion, a first suture end portion for attachment to a suture and a second needled end portion for penetrating tissue. The needled end portion has three sides which intersect to define three cutting edges and terminate at a needle point. At least one side includes a pair of planar surface portions arranged in oblique relation to define a general concave appearance to the one surface. The needled end portion further defines an enlarged transition portion disposed adjacent the central shaft section and having an x-dimension which is at least substantially equal to, preferably, greater than, a corresponding x-dimension of the central shaft portion. Preferably, each of the three sides includes the planar surface portions arranged in oblique relation to define a general concave appearance to the respective side.

The enlarged transition portion may define a z-dimension at least substantially equal to, preferably, greater than, a corresponding z-dimension of the central shaft portion. The x-dimension and z-dimension correspond to the height and width respectively of the needle end portion.

The planar surface portions of the one side intersect to define an included angle ranging from about 160° to about 175°. One preferred included angle is about 170°. Two of the cutting edges intersect at the needle point and define an angle of about 16° to about 25°.

The central shaft portion defines a distal shaft transition portion adjacent the needled end portion. The distal shaft portion defines a cross-section of general triangular character. The distal shaft portion includes three planar surfaces interconnected by rounded surfaces.

In another preferred embodiment, the surgical needle, includes an elongated needle body defining a longitudinal y-axis along which the needle body extends and transverse x and z-axes. The needle body includes a central shaft portion, a first suture end portion for attachment to a suture and a second needled end portion for penetrating tissue. The needled end portion has three sides which intersect to define three edges and terminate at a needle point. Each of the sides includes a pair of planar surface portions arranged in oblique relation to define a general concave appearance to the one side. The needled end portion further defines an enlarged transition portion adjacent the central shaft section with an x-dimension at least substantially equal to a corresponding x-dimension of the central shaft. Preferably, the enlarged transition portion defines an x-dimension greater than a corresponding x-dimension of the central shaft portion. The enlarged transition portion may further define a z-dimension at least substantially equal to a corresponding z-dimension of the central shaft. Preferably, z-dimension of the enlarged transition portion is greater than a corresponding z-dimension of the central shaft portion.

BRIEF DESCRIPTION OF THE DRAWINGS

The accompanying drawings, which are incorporated in and constitute a part of this specification, illustrate embodiments of the disclosure and, together with a general description of the disclosure given above, and the detailed descrip tion of the embodiments given below, serve to explain the principles of the disclosure.

FIGS. 6-7 are top and bottom perspective views, respectively, of the needled end portion;

FIG. 8 is an enlarged cross-sectional view of the needled end portion taken along the lines 8-8 of FIG. 4;

FIG. 9 is an isolated view of FIG. 8 illustrating details of a cutting surface of the needled end portion; and FIGS. 10A-10B are isolated views illustrating details of cutting surfaces of alternate embodiment(s) of the needled end portion.

BRIEF DESCRIPTION OF PREFERRED EMBODIMENTS

Figure 1:
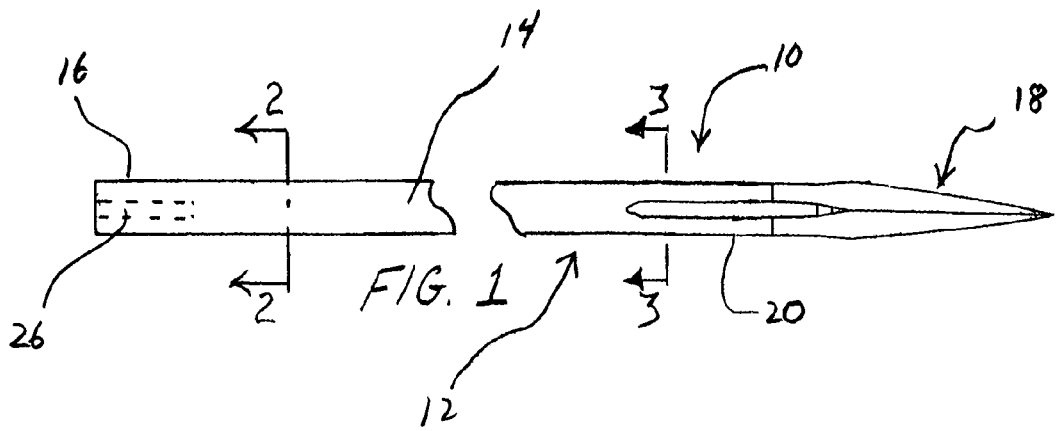
FIG. 1 is a top plan view of the surgical needle in accordance with the principles of the present disclosure, illustrating the central shaft, the suture end portion and the needle end portion of the needle.

Preferred embodiment(s) of the surgical needle of the present disclosure will now be described in detail with reference to the drawings wherein like reference numerals identify similar or like elements throughout the several views. As used herein, the term "distal" refers to that portion which is further from the user, while the term "proximal" refers to that portion which is closest to the user.

Figure 2:
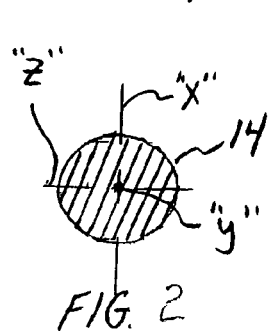
FIG. 2 is an enlarged cross-sectional view taken along the lines 2-2 of FIG. 1 illustrating the dimensioning of the central shaft of the needle.
Figure 3:
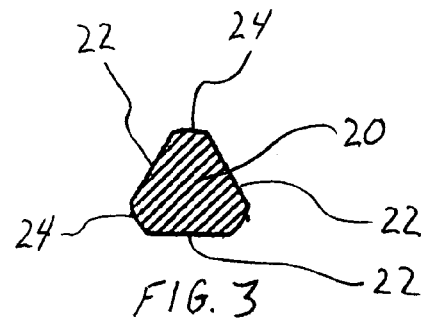
FIG. 3 is an enlarged cross-sectional view taken along the lines 3-3 of FIG. 1 illustrating the dimensioning of the central shaft at a location adjacent the needled end portion.

With reference now to FIGS. 1-3, the surgical needle 10 of the present disclosure is illustrated. Surgical needle 10 includes elongated needle body 12 which defines longitudinal axis "y" extending along the length of needle body 12 and transverse axes "x" and "z". Transverse axes "x" and "z" correspond to the height and width dimensions of needle body 12, respectively. Needle body 12 includes central shaft 14, first or suture end portion 16 adjacent one end of the central shaft 14 and second or needled end portion 18 adjacent the other end of the shaft 18. Central shaft 14 is shown as straight in FIG. 1, however, it is appreciated that central shaft 14 may be curved through an arc of curvature to provide a curved needle 12.

Central shaft 14 is circular in cross-section (FIG. 2) along most of its length with the exception of shaft section 20 adjacent needled end portion 18. Alternatively, central shaft 14 may be triangular, rectangular, double-D shaped or oval-shaped in cross-section. Central shaft 14 provides a symmetrical profile to facilitate gripping engagement by the user with a needle holder, e.g., needle forceps, and manipulation about the operative site. As best depicted in FIG. 3, shaft section 20 is generally triangular in cross-section characterized by having three planar surfaces 22 joined along respective curved edges 24. Curved edges 24 provide an atraumatic surface to minimize tissue trauma subsequent to passage of needled end portion 18. Shaft section 20 may also be square, rectangular, oval or double-D shaped in cross-section.

Suture end portion 16 defines an elongated enclosed aperture 26 (shown in phantom in FIG. 1) dimensioned for reception of a suture end. Aperture 26 is preferably closed through a swaging or crimping process about the suture end to securely engage and attach the suture end to needle body 12. Suitable apparatii and associated methods for effecting needle suture attachment are disclosed in commonly assigned U.S. Pat. No. 5,568,746 to Colligan et al. and U.S. Pat. No. 5,383,902 to Carpentiere et al., the contents of each being incorporated herein by reference. Alternatively, suture end portion 16 may include an open U-shaped channel for reception of the suture end. Adhesive methodologies for effecting needle-suture attachment are also envisioned.

Figure 4:
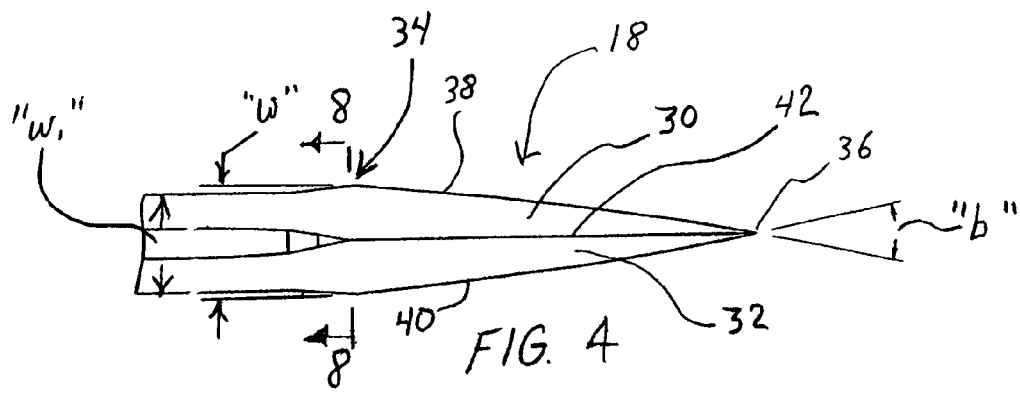
FIG. 4 is an enlarged top plan view of the needled end portion of the needle.
Figure 5:
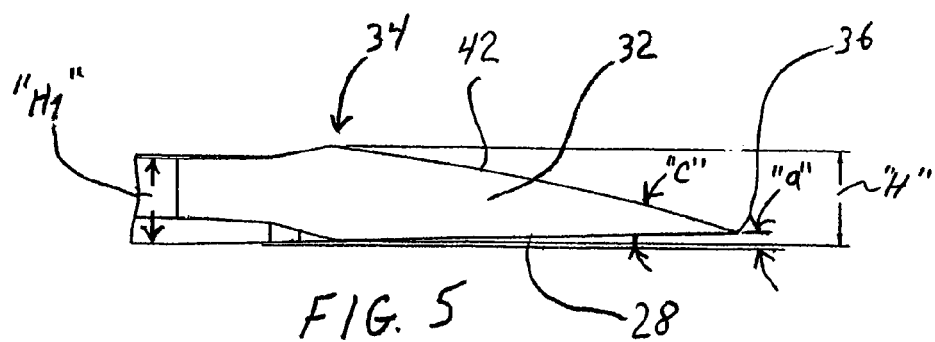
FIG. 5 is an enlarged side plan view of the needled end portion.

Referring now to FIGS. 4-7, in conjunction with FIG. 1, needled end portion 18 of needle 10 will be discussed in detail. Needled end portion 18 defines an enlarged needle head advantageously dimensioned to optimize its penetration capabilities through tissue and to minimize the effect of tissue drag. Needled end portion 18 includes three surfaces 28, 30, 32 which gradually taper inwardly relative to longitudinal axis "y" from enlarged transition portion 34 and terminate in needle point 36. (For descriptive purposes, surface 28 will be referred to hereinafter as lower surface 28 and surfaces 30, 32 will be referred to as upper surfaces 30, 32.) Lower surface 28 is substantially parallel to longitudinal axis "y" extending at a relatively small oblique angle "a" (FIG. 5) relative to the axis "y". Angle "a" preferably ranges between about 2° to about 10. Consequently, needle point 36 is displaced in the x-direction (relative to transverse x-axis) toward lower surface 28 as best depicted in FIG. 5.

Upper surfaces 30, 32 intersect lower surface 28 along side edges 38, 40 and intersect each other along upper edge 42. Edges 38, 40, 42 may be arranged as to define cutting edges. Side cutting edges 38, 40 intersect at needle point 36 to define an angle "b" (FIG. 4) which preferably ranges from about 22° to about 26°, most preferably about 24°. Upper cutting edge 42 intersects lower surface 28 at needle point 36 to define an included angle "c" (FIG. 5) ranging from about 5° to about 40°, most preferably 25°. As appreciated, the angular arrangements of cutting edges 38, 40 and 42 define a relatively sharp needle point 36 capable of penetrating tissue with minimal force.

With reference now to FIGS. 8-9, taken in conjunction with FIG. 4, each surface 28, 30, 32 includes a pair of surface portions 44 which intersect along a median plane "m" intersecting each surface 28, 30, 32 at a large oblique angle "d" relative to each other. (FIG. 9) The preferred angle of intersection "d" ranges from about 160° to about 175°, most preferably 170°. The intersecting surface portions 44 thus provide an overall concave or hollow ground appearance to the respective surfaces 28, 30, 32. This concave effect provides significant advantages in passage of the needle 10 through tissue. Specifically, the reduction in cross-section of needled end portion 18 provided by the inclined surface portions 44 of each surface 28, 30, 32 significantly reduces tissue drag compared to a conventional flat sided triangular-shaped needle head.

Referring now to FIGS. 4-5 and 8, the dimension of needled end portion 18 is greatest at transition portion 34. Specifically, transition portion 34 defines a maximum height "H" (along the x-axis) and a maximum width "W" (along the z-axis) which are at least equal to, preferably, greater than the corresponding height and width of distal shaft section 20, and greater than the diameter of central shaft 18. Preferably, the ratio of the maximum height "H" of transition portion 34 to the height "$H_1$" of distal shaft section 20 ranges from about 1.1 to about 1.4, and the maximum width "W" to the width "$W_1$" of distal shaft section ranges from about 1.0 to about 1.2.

FIGS. 10A-10B illustrate alternate embodiments where only one of the surfaces 28, 30, 32 includes the intersecting inclined surface portions 44. The remaining two of the surfaces 28, 30, 32 may be planar (FIG. 10A) or concave (FIG. 10B) in configuration, or a combination of planar and concave (i.e., one of the remaining two surfaces 28, 30, 32 is planar and the other is concave).

The surgical suturing needle of the present disclosure possesses attributes of primary significance in suturing needles. Specifically, the suturing needle of the present disclosure exhibits superior needle sharpness to facilitate penetration and relatively easy passage through cutaneous and subcutaneous layers of tissue. In particular, the narrowed triangular cross-sectional dimension and cutting edges 38, 40, 42 of needled end portion 18 produce a sharpened profile which significantly reduces the penetration force required to penetrate the body tissue. Cutting edges 38, 40, 42 extend to transition portion 34 of needled end portion 18 thereby slicing the tissue as it passes through and providing an opening which is slightly larger than the cross-section of central shaft 18, consequently, significantly reducing the drag force and permitting the shaft 18 to easily pass through the tissue. As indicated hereinabove, drag force is further minimized through the concave appearance of surfaces 28, 30, 32 (as effected by inclined surface portions 44 of each surface) and consequent reduced cross-sectional dimension thereby provided. Drag force may be further reduced with a suitable lubricious coating such as the silicone coating disclosed in U.S. Pat. No. 5,458,616 to Granger, the contents of which are incorporated herein by reference.

The surgical needle of the subject disclosure also demonstrates superior strength and resistance to bending and/or breaking during use. The choice of materials of surgical needle 10 is made to optimize strength, ductility and resistance to bending or breaking of the needle. Preferred materials include stainless steel such as series "300" stainless steels, which typically have tensile strengths of between 325,000-350,000 lbs/in.sup.2, attain their high strength from undergoing cold working as the material is converted from an ingot to wire of the desired diameter.

Surgical needle 10 is manufactured through conventional cutting, coining, grinding and/or swaging processes, and may be heat treated to further enhance its strength and resistance to bending. Sutures for attachment to surgical needle 10 include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical needle, which comprises:
an elongated substantially linear needle body defining a central longitudinal y-axis along which the needle body extends and transverse x and z-axes, the needle body including a central shaft portion, a first suture end portion for attachment to a suture and a second needled end portion for penetrating tissue, the needled end portion having three sides which intersect to define three cutting edges and terminate at a needle point, each side including one sole pair of planar surface portions arranged in oblique relation to define a general concave appearance to each side, the needled end portion further defining an enlarged transition portion adjacent the central shaft section, the enlarged transition portion defines a z-dimension "$z_1$" and an x-dimension "$x_t$", "$x_t$" being greater than a corresponding x-dimension "$x_1$" of the central shaft, wherein the z-dimension "$z_t$" is defined as being transversely perpendicular to the central longitudinal y-axis and extending between a first cutting edge and a second cutting edge, and wherein the x-dimension "$x_t$" is defined as being offset 90° from the z-dimension "$z_1$" and extending between a third cutting edge and a surface portion between the first cutting edge and the second cutting edge;
the needle point being displaced a predetermined distance with respect to the longitudinal axis and wherein the predetermined distance is less than ½ the x-dimension "$x_t$" of the enlarged transition portion; and
at least one side of the needled end portion being displaced in the x-dimension "$x_t$" by an angle α from a plane parallel to the longitudinal axis, the angle α being between about 2° and 10°, wherein the side of the needled end portion displaced by angle α from the plane parallel to the longitudinal axis has a substantially continuous slope between the enlarged transition portion and the needle point.

2. The surgical needle according to claim 1 wherein the planar surface portions of each side are arranged to intersect along a median plane bisecting a respective side to define a substantially symmetrical concave appearance to the respective side.

3. The surgical needle according to claim 1 wherein the enlarged transition portion defines a z-dimension "$z_t$" greater than a corresponding z-dimension "$z_1$" of the central shaft portion.

4. The surgical needle according to claim 3 wherein the x-dimension "$x_t$" and the z-dimension "$z_1$" correspond to the height and width respectively of the transition portion of the needled end portion.

5. The surgical needle according to claim 1 wherein the planar surface portions of each side intersect to define an included angle ranging from about 160° to about 175°.

6. The surgical needle according to claim 5 wherein the included angle is about 170°.

7. The surgical needle according to claim 1 wherein two of the cutting edges intersect at the needle point and define an angle of about 22° to about 25°.

8. The surgical needle according to claim 1 wherein the central shaft portion defines a distal shaft transition portion adjacent the needled end portion, the distal shaft portion defining a cross-section or general triangular character.

9. The surgical needle according to claim 8 wherein the distal shaft portion includes three planar surfaces interconnected by rounded surfaces.

10. The surgical needle according to claim 1 wherein each cutting edge is substantially linear.

11. The surgical needle according to claim 1 wherein the needle body is adapted to assume a curved configuration.

12. A surgical needle, which comprises:
an elongated needle body defining a central longitudinal y-axis along which the needle body extends and transverse x and z-axes, the needle body including a central shaft portion, a first suture end portion for attachment to a suture and a second needled end portion for penetrating tissue, the needled end portion having three sides which intersect to define three cutting edges and terminating at a needle point, each side including a pair of planar surface portions arranged in oblique relation and intersecting along a median plane bisecting a respective side to define a general concave appearance to the respective side, the needled end portion further defining an enlarged transition portion adjacent the central shaft section;

wherein the enlarged transition portion defines a z-dimension "$z_t$" and an x-dimension "$x_t$", "$x_t$" being greater than a corresponding x-dimension "$x_1$" of the central shaft, wherein the z-dimension "$z_t$" is defined as being transversely perpendicular to the central longitudinal y-axis and extending between a first cutting edge and a second cutting edge, and wherein the x-dimension "$x_t$" is defined as being offset 90° from the z-dimension "$z_t$" and extending between a third cutting edge and a surface portion between the first cutting edge and the second cutting edge;

the needle point being displaced a predetermined distance with respect to the longitudinal axis and wherein the predetermined distance is less than ½ the x-dimension "$x_t$" of the enlarged transition portion; and at least one side of the needled end portion being displaced in the x-dimension "$x_t$" by an angle α from a plane parallel to the longitudinal axis, the angle α being between about 2° and 10°, wherein the side of the needled end portion displaced by angle α from the plane parallel to the longitudinal axis has a substantially continuous slope between the enlarged transition portion and the needle point.

13. The surgical needle according to claim 12 wherein the enlarged transition portion "$z_t$" at least substantially equal to a corresponding z-dimension "$z_1$" of the central shaft.

14. The surgical needle according to claim 13 wherein the enlarged transition portion "$z_t$" is greater than the corresponding z-dimension "$z_1$" of the central shaft portion.

15. The surgical needle according to claim 14 wherein each side of the needled end portion includes a single pair of first and second planar surface portions arranged in oblique relation, the first and second planar portions being the pair of planar portions.

16. The surgical needle according to claim 12 wherein each side of the needled end portion includes a single pair of first and second planar surface portions arranged in oblique relation, the first and second planar portions being the pair of planar portions.

17. The surgical needle according to claim 12 wherein each cutting edge is substantially linear.

* * * * *